United States Patent [19]

Peterson et al.

[11] Patent Number: 5,670,377

[45] Date of Patent: Sep. 23, 1997

[54] METHOD OF DIAGNOSING GESTATIONAL DIABETES

[75] Inventors: Charles M. Peterson; Lois G. Peterson, both of Santa Barbara, Calif.

[73] Assignee: Sansum Medical Research Foundation, Santa Barbara, Calif.

[21] Appl. No.: 615,973

[22] Filed: Mar. 14, 1996

[51] Int. Cl.$^6$ .................................................. G01N 33/50
[52] U.S. Cl. ............................ 436/87; 436/95; 436/811
[58] Field of Search .......................... 436/87, 88, 95, 436/811

[56] References Cited

U.S. PATENT DOCUMENTS

| | | | |
|---|---|---|---|
| 4,956,301 | 9/1990 | Ismail et al. | 436/87 |
| 5,187,154 | 2/1993 | Phillips et al. | 514/12 |

OTHER PUBLICATIONS

Hidetsugu, N. "Studies on Glycosylated Protein During Pregnancy with Glyc Affin System" Igaku Kenkyu (Acta Medica), vol. 57, No. 2 (1987) pp. 105–115.

Schrader H.M. "Fasting Plasma–Glucose and Glycosylated Plasma–Protein at 24–28 Weeks of Gestation Predict Macrosomia in the General Obstetric Population" American Journal of Perinatology, vol. 12, No. 4, (Jul. 1995), pp. 247–251.

Cefalu, W.T. et al. "Total Serum Glycosylated Proteins in Detection and Monitoring of Gestational Diabetes" Diabetes Care, vol. 13 (1990) pp. 872–875.

Skyler, J.S. et al. "Blood Glucose Control During Pregnancy" Diabetes Care, vol. 3, (1980) pp. 69–76.

Jovamovic, L. et al. "Screening for Gestational Diabetes Optimum Timing and Criteria for Retesting" Diabetes, vol. 34, Supplement 2 (1985) pp. 21–23.

Little et al.; Lack of relationship between glucose tolerance and complications of pregnancy in nondiabetic women; Diabetes Care, vol. 13, No. 5, May 1990.

Rodriquez et al.; Screening adolescent gravidas for gestational diabetes; Adolesc. Pediatr. Gyn. (1995) 8:125–127.

Schwartz et al.; Goycosylated hemoglobin assays in the management and diagnosis of diabetes mellitus; Annals of Internal Medicine, 1984; 101:710–713.

Miller et al.; Elevated maternal hemoglobin $A_{1c}$ in early pregnancy and major congenital anomalies in infants of diabetic mothers.

Rizvi et al.; Plasma glucose control in pregnancy complicated by chemical diabetes; J. of Obstetrics and Gynecology; vol. 87, pp. 383–387.

Watkins; Congential malformations and blood glucose control in diabetic pregnancy; British Medical Journal;. London, Saturday, May 8, 1992.

Kjzergaard et al.; Hemoglobin $A_{1c}$ as an indicator of long term blood glucose levels i daibetics with special reference to diabetic pregnancy; Endocrinologica 1980, 94:Suppl. 238:25–29.

Kjaergaard et al.; Hemoglobin $A_{1c}$ as an index of long term blood glucose regulation in diabetic pregnancy; Diabetes, vol. 28, Jul. 1979.

Widness et al.; Hemoglobin $A_{1c}$ Glycohaemoglobin in diabetic pregnancy: Aninidicator of glucose control and fetal size; British J. of Obstetrics and Gynecology; Nov. 1978, vol. 85, pp. 812–817.

Madsen et al.; Hemoglobin $A_{1c}$ determinations in diabetic pregnancy; Diabetes Care, vol. 4, No. 5, 1981.

Schwartz et al.; Effects of Pregnancy on Hemoglobin $A_{1c}$ in Normal, Gestational Diabetic, and Diaetic Women; Diabetes, vol. 25, No. 12, 1976.

Shah et al.; Comparison of glycohemoglobin determination and the one–hour oral glucose screen in the identification of gestational diabetes; Dec., 1982, Am. J. Obstet. Gynec., pp. 774–777.

Worner et al.; Selective determination of non–enzymatic glycosylatd serum albumin as a medium term index of diabetic control; Internat'l Journal of Clinical Pharmacology, Therapy and Toxicology, vol. 31, No. 5 1992 (218–222).

Gordon et al.; Glycosylated serum protein levels assayed with highly sensitive immunoradiometric assay accurately reflect glycemic control of diabetic patients; Diabetes Care, vol. 15, No. 5, May 1992.

Fadel et al.; Glycosylated hemoglobins in normal pregnancy and gestatinoal diabetes mellitus; Obstetrics & Gynecology; vol. 54, No. 3, Sep. 1979.

O'Shaughnessy et al.; Glycosylated hemoglobins and diabetes mellitus in pregnancy; Am. J. Obstet. Gynecol., Nov. 15, 1979.

(List continued on next page.)

*Primary Examiner*—Jeffrey Snay
*Attorney, Agent, or Firm*—Hovey, Williams, Timmons & Collins

[57] ABSTRACT

Methods of diagnosis of gestational diabetes mellitus are disclosed. In preferred embodiments, a blood sample is obtained from a pregnant female in the 24th to 28th week of pregnancy after an overnight fast, after a 1-hour 50-gram glucose challenge test, or at the 1-hour time point during a 3-hour 100-gram oral glucose tolerance test. The concentrations of fasting plasma glucose and glycosylated plasma proteins in this blood sample are then determined. A fasting plasma glucose concentration equal to or exceeding 90 mg/dL is 100% sensitive and 64% specific in predicting glucose-related macrosomia (i.e., birth weight above 4000 grams). A glycosylated plasma protein concentration equal to or exceeding 23% is 100% sensitive and 52% specific in predicting glucose-related macrosomia. A fasting plasma protein value equal to or exceeding 90 mg/dL and a glycosylated plasma protein value equal to or exceeding 23% is 100% sensitive and 93% specific in predicting glucose-related macrosomia.

24 Claims, 1 Drawing Sheet

OTHER PUBLICATIONS

Tahara et al.; The response of GHb to stepwise plasma glucose change over time in diabetic patients; Diabetes Care. vol. 16, No. 9, Sep., 1993.

Mayer et al.; Protein glycosylation in diabetes mellitus: a review of laboratory measurements and oftheir clinical utility; Clinica Chimica Acta 127 (1983) 147–184.

Santiago et al.; Hemoglobin $A_{1c}$ levels in a diabetes detection program; J. Clinical Endocrinology and Metabolism; vol. 47, No. 3, 1978.

Parfitt et al.; Use of fructosamine and glycated Haemoglobin to verify self blood glucose monitoring data in diabetic pregnancy; Diabetic Medicine, 1993; 10:162–166.

Shields et al.; The prognostic value of hemoglobin A1c in predictin fetal heart disease in diabetic pegnancies; Obstetrics & Gynecology; vol. 81, No. 6, Jun. 1993.

METHOD OF DIAGNOSING GESTATIONAL DIABETES

BACKGROUND OF THE INVENTION

1. Field of the Invention

The present invention is broadly concerned with methods of diagnosing gestational diabetes mellitus (GDM). More particularly, in these methods, the concentrations of fasting plasma glucose (FPG) and glycosylated plasma protein (GPP) in the blood of a female in the 24th to 28th week of pregnancy are determined; concentrations of FPG and GPP equal to or exceeding 90 mg/dL and 23%, respectively, indicate that the pregnant female may be suffering from GDM and is therefore at risk of giving birth to a macrosomic infant.

2. Description of the Prior Art

GDM is defined as carbohydrate intolerance of variable severity with first onset during pregnancy (1). GDM affects 2 to 12% of all pregnant women (2). If undiagnosed, GDM may cause a variety of maternal-fetal complications. The most common of these complications is macrosomia, defined as a birth weight greater than the 90th percentile for gestational age (3). Macrosomic fetuses are at a high risk for birth traumas, neonatal hypoglycemia, and other complications associated with GDM (4, 5). An increased risk of macrosomia also may be present in women having only minor elevations in glucose levels (6). The prevalence of macrosomia in the Santa Barbara County Health Care Services has dropped from 18% in 1984–1985 to 7% in 1991–1992 since introduction of universal screening for GDM. Nevertheless, infants unsuspectedly large for their gestational age still occur in low-risk pregnancies because prior-art screening tests are not sensitive enough to detect women at risk for delivering macrosomic infants.

Measurement of glycosylated hemoglobin (GHb) levels, a single test and an indicator of long-term glucose control, lacks the sensitivity needed to screen for GDM, let alone milder elevations of glucose levels (7, 12). Therefore, it is unlikely that GHb is useful in screening for macrosomia. The studies on the use of GHb to predict macrosomia have been controversial and generally are retrospective, with measurement of GHb levels performed at delivery (24, 25). Studies on the use of glycosylated albumin, glycosylated serum protein (GSP), and fructosamine (8–14) have shown that these glycosylated proteins are not useful indicators of GDM.

Some researchers have examined glucose concentrations determined on the glucose challenge test (GCT) and the oral glucose tolerance test (OGTT) to predict macrosomia (6, 15, 26–29). Sacks et al. (15) reported that the fasting blood glucose concentration on the OGTT performed in those women with a positive GCT correlated with macrosomia. Magee et al. (27) found that the frequency of macrosomia was 27% in women who screened negative on the GCT, 19% in women who screened positive on the GCT and negative on the OGTT, and 27% in women who screened positive on the GCT and on the OGTT. Little and coworkers (28) found that FPG concentrations and 2-hour plasma glucose concentrations on the OGTT were higher in those mothers who delivered an infant large for gestational age. Jovanovic and Peterson (6) showed that an elevated 1-hour plasma glucose concentration on the GCT correlated with an increased risk of macrosomia despite normal results on the OGTT. Skyler and coworkers (29) showed that a FPG concentration above 90 mg/dL increased the risk for macrosomia.

Glucose-mediated macrosomia and the associated fetopathy of hypoglycemia, respiratory distress, hyperbilirubinemia, erythremia, and hypocalcemia are preventable if hyperglycemia is identified early in a pregnancy and treatment designed to normalize blood glucose levels is instituted (18, 19). However, the traditional methods for screening and diagnosis of GDM do not detect all infants at risk for glucose-related macrosomia (14, 20–23).

SUMMARY OF THE INVENTION

The present invention overcomes the problems outlined above by providing methods of detecting infants at risk for glucose-related macrosomia in the nondiabetic population. Furthermore, these methods can employ a single blood sample obtained from a pregnant female. In preferred embodiments, a blood sample is obtained from a pregnant female in the 24th to 28th week of pregnancy after an overnight fast, after a 1-hour 50-gram GCT, or at the 1-hour time point during a 3-hour 100-gram OGTT. The concentrations of FPG and/or GPP are determined by a hexokinase method and by boronate-affinity high-performance liquid chromatography, respectively. Advantageously, the concentration of GPP can be determined using a blood sample drawn at any time, and the concentrations of FPG and GPP can be determined using different blood samples. The concentration of FPG is expressed as a weight of FPG per volume of blood plasma, and the concentration of GPP is expressed as the percentage of total plasma protein that is glycosylated. An FPG concentration equal to or exceeding 90 mg/dL is 100% sensitive in predicting birth weight above 4000 grams; however, this test has a specificity of only 64% (i.e., gives 36% false positives). A GPP concentration equal to or exceeding 23% is also 100% sensitive in predicting birth weight above 4000 grams; however, this test is only 52% specific. Using a combination of an FPG concentration equal to or exceeding 90 mg/dL and a GPP concentration equal to or exceeding 23% results in 100% sensitivity and 93% specificity in predicting birth weight above 4000 grams. If GDM is detected based on the results of these methods, a treatment designed to normalize blood glucose levels should be administered to the pregnant female to prevent glucose-mediated macrosomia.

DETAILED DESCRIPTION OF THE PREFERRED EMBODIMENT

Example

Figure 1:
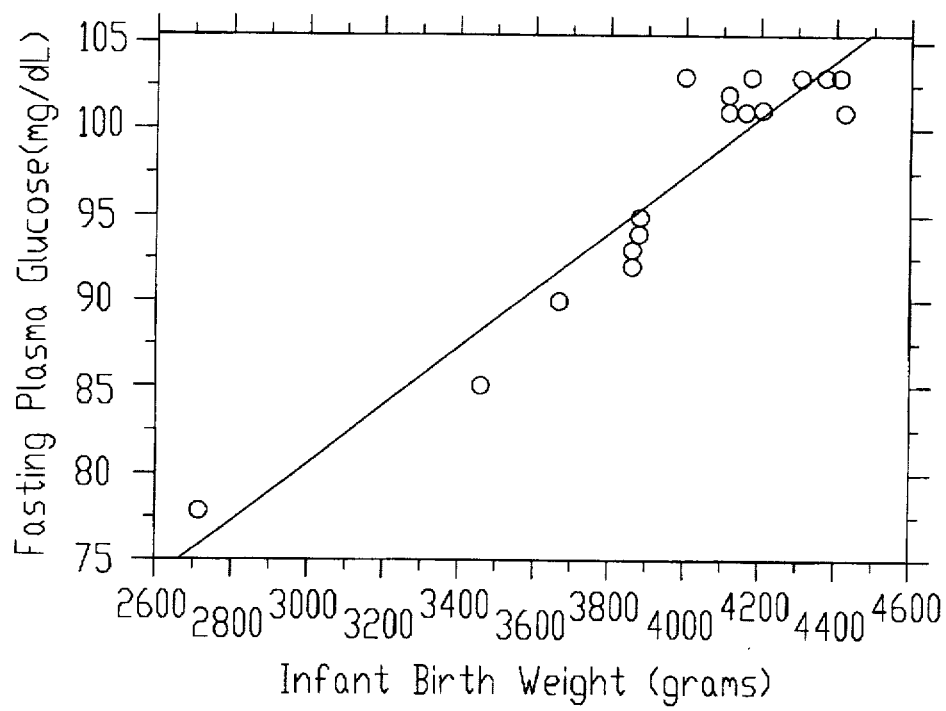
FIG. 1 is a regression plot illustrating the correlation of FPG concentrations (mg/dL) on the OGTT and infant birth weight (g)

The following example describes methods of diagnosing GDM. The example is set forth by way of illustration only and nothing therein shall be taken as a limitation upon the overall scope of the invention.

METHODS AND MATERIALS

In an obstetrics clinic, 160 pregnant women at 24 to 28 weeks' gestation were given a 1-hour 50-gram GCT according to the recommendation of the Third International Gestational Diabetes Workshop (1). If this glucose challenge resulted in a plasma glucose concentration greater than 140 mg/dL, the patient underwent a formal 3-hour 100-gram OGTT after an overnight fast (1). All blood glucose concentrations were determined in the Santa Barbara County Health Services laboratories using a hexokinase method (Boehringer-Mannheim-Hitachi Systems, Indianapolis, Ind.). At the time of the GCT, two additional tubes of blood were drawn at the 1-hour time point for determination of GSP, GPP, and GHb concentrations by boronate-affinity high-performance liquid chromatography (Primus, Kansas City, Mo.). The normal concentration range is 13.0 to 21.0% for GSP, 17.0 to 23.6 for GPP, and 4.1 to 6.1% for GHb. Inter- and intra-assay levels of precision (coefficients of variation) for each assay were less than 3%. For example, with a maximum coefficient of variation of 3% for a GPP concentration of 20%, the coefficient of variation is ±0.6% with a range of 19.4 to 20.6%.

The patients' charts were reviewed on completion of the pregnancies at various hospitals and clinics in Santa Barbara County. Infant birth weight, ethnic background, length, gender, and gestational age at delivery were recorded. Of the 160 infants, 148 were of Mexican-American origin, and gestational age at delivery was 39 to 41 weeks in all cases. The 90th percentile birth weight in California for Mexican-American boys at this gestational age is 4100 grams and for Mexican-American girls is 3990 grams (16). Thus, the cutoff for macrosomia of 4000 grams was used for the analysis of the entire cohort.

None of the GCT-negative or the GCT-positive-OGTT-negative patients received intervention for glycemic control. All of the OGTT-positive patients received treatment as defined previously (1) and therefore these data were excluded from the analysis. StatView 4.0 (Abacus Concepts, Berkeley, Calif.) was used for statistical analysis.

RESULTS

Of the 160 women screened for GDM, 11 (7%) subsequently gave birth to macrosomic infants. Twenty-three women had a positive GCT (14.4%) and five were diagnosed as gestational diabetic women (3.13%), as already defined. The infants born of these five gestational diabetic women were excluded from the analysis because they received treatment designed to impact on infant birth weight.

Table 1 summarizes correlations from the GCT and OGTT (glucose and glycosylated proteins). As can be seen, the 1-hour plasma glucose concentration on the GCT was significantly related to the GPP concentration ($p<0.001$; $r=0.37$) and the GHb concentration ($p<0.001$; $r=0.35$), but not the GSP concentration. The glycosylated proteins also correlated positively with certain values on the OGTT, for example, GPP concentration versus FPG concentration ($p<0.01$; $r=0.56$); GHb concentration versus the 1-hour plasma glucose concentration ($p=0.018$; $r=0.50$). Of note, the GSP concentration related to the GPP concentration with a $p<0.001$ and an $r=0.31$; however, GHb concentration did not correlate significantly with either the GSP concentration or the GPP concentration.

Table 2 contains those variables from the GCT and OGTT that correlated with subsequent infant birth weight. As can be seen, the FPG concentration on the OGTT correlated most strongly with birth weight ($p<0.001$; $r=0.94$). The relationship of the GPP concentration and subsequent infant birth weight was also significant ($p<0.001$; $r=0.81$). Other variables obtained during the GCT that significantly correlated with birth weight included the 1-hour plasma glucose concentration on the GCT ($p<0.001$; $r=0.51$) and the GHb concentration ($p=0.001$; $r=0.37$).

As shown in FIG. 1, the FPG concentration on the OGTT significantly correlated with birth weight ($r=0.937$; $p<0.001$). An FPG concentration greater than 90 mg/dL correctly identified all the potential macrosomic infants (birth weight greater than 4000 grams). Only nine macrosomic infants were in this group because two women had a macrosomic infant but did not have a positive GCT and thus an OGTT was not ordered. Five mothers with an FPG concentration greater than 90 mg/dL delivered an infant of normal weight, but these five women all delivered infants who weighed greater than 3800 grams. Thus, a 90 mg/dL cutoff for FPG concentration is 100% sensitive and 64% specific (but 100% specific for predicting women who will deliver an infant who weighs greater than 3800 grams).

Figure 2:
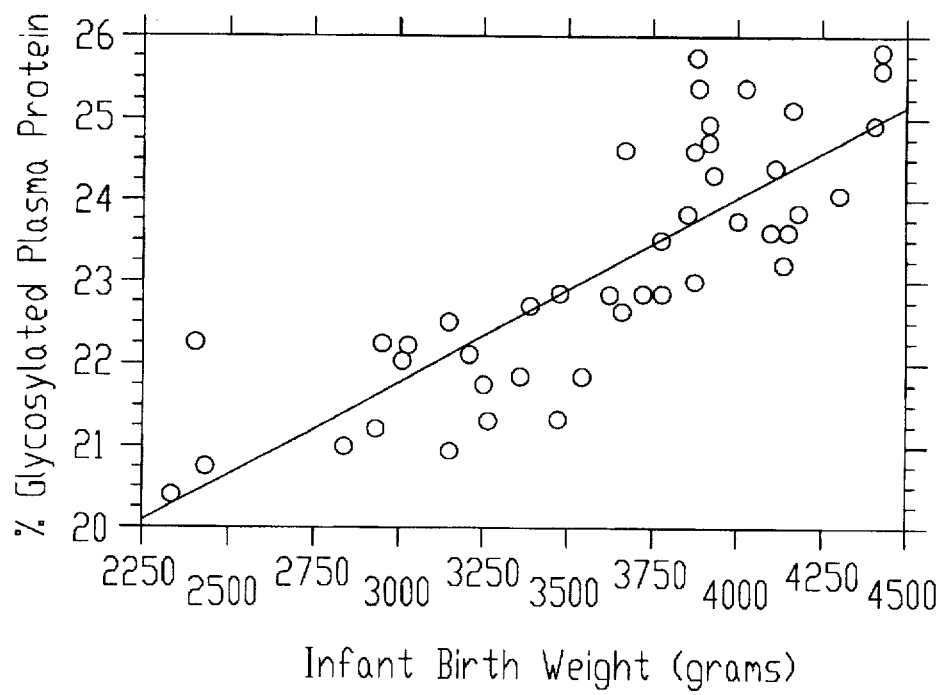
FIG. 2 is a regression plot illustrating the correlation of GPP concentrations (%) on the OGTT and infant birth weight (g).

As shown in FIG. 2, GPP concentration was also significantly correlated with birth weight ($r=0.814$, $p<0.001$). In fact, each of 11 mothers who gave birth to an infant weighing greater than 4000 grams had a GPP concentration equal to or greater than 23%. However, 10 full-term infants delivered of mothers with a GPP concentration greater than 23% were of normal weight, thus giving 10 false-positive results; however, eight of these infants weighed greater that 3800 grams. Therefore, using this cutoff, the GPP test also is 100% sensitive for all macrosomic infants, yet shows only 52% specificity for predicting those women who will deliver an infant who weighs more than 4000 grams (but 89% specificity for infants weighing greater than 3800 grams).

When the combination of a GPP concentration greater than 23% and an FPG concentration greater than 90 mg/dL was analyzed as two necessary criteria, all 11 macrosomic infants were identified. However, three of the mothers with a GPP concentration, above 23% who delivered a normal weight infant had an FPG concentration below 90 mg/dL. Thus, the combination of a GPP concentration above 23% and a FPG concentration above 90 mg/dL is associated with macrosomia with 100% sensitivity and 93% specificity.

Because FPG concentration and GPP concentration are probably interdependent variables that correlate well with each other ($r=0.56$; $p<0.01$), their respective correlations with infant birth weight might simply reflect their interdependence. Partial correlation coefficients (17) that take into account the potential interdependence of FPG concentration and GPP concentration showed that, although the two variables were related to each other, the stronger relationship for each was with infant birth weight. The partial correlation with infant birth weight was 0.59 ($p=0.015$) for GPP concentration and 0.90 ($p<0.001$) for FPG concentration.

TABLE 1

| Correlation of the Variables with Each Other[a,b] | | | |
|---|---|---|---|
| Variable (Means ± SD) | Versus Variable (Means ± SD) | p Value | r Value |
| 1-h GCT (108.4 ± 31.2) | 3-h OGTT (134.9 ± 119.5) | 0.000 | 0.773 |
|  | GPP (22.6 ± 1.48) | 0.000 | 0.366 |
|  | GHb (5.23 ± 0.76) | 0.000 | 0.350 |
|  | 1-h (149.9 ± 39.8) | 0.078 | 0.389 |
|  | 2-h (130.95 ± 23.03) | 0.525 | 0.147 |
|  | FPG (94.83 ± 8.26) | 0.532 | 0.137 |
| 0-h OGTT (94.83 ± 8.26) | 1-h (149.9 ± 39.8) | 0.147 | 0.289 |
|  | 3-h (134.9 ± 119.5) | 0.430 | 0.187 |
|  | 2-h (130.95 ± 23.0) | 0.471 | 0.171 |
| 1-h OGTT (149.9 ± 39.8) | 2-h OGTT (130.9 ± 23.0) | 0.025 | 0.489 |
|  | 3-h (134.9 ± 119.5) | 0.426 | 0.184 |
| 2-h OGTT (130.95. ± 23.03) | 3-h (134.9 ± 119.5) | 0.804 | 0.058 |
| GHb (5.23 ± 0.76) | 1-h OGTT (145.0 ± 39.76) | 0.018 | 0.501 |

TABLE 1-continued

Correlation of the Variables with Each Other[a,b]

| Variable (Means ± SD) | Versus Variable (Means ± SD) | p Value | r Value |
|---|---|---|---|
| | 3-h OGTT (134.9 ± 119.5) | 0.063 | 0.416 |
| | GPP (22.56 ± 1.48) | 0.076 | 0.151 |
| | 0-h OGTT (94.83 ± 8.26) | 0.141 | 0.282 |
| | 2-h OGTT (130.95 ± 23.03) | 0.412 | 0.189 |
| GPP (22.6 ± 1.48) | GSP (17.04 ± 1.187) | 0.000 | 0.308 |
| | 0-h OGTT (94.83 ± 8.26) | 0.009 | 0.558 |
| | 3-h OGTT (134.9 ± 119.5) | 0.143 | 0.330 |
| | 2-h OGTT (130.95 ± 23.03) | 0.521 | 0.162 |
| GSP (17.04 ± 1.19) | 2-h (130.95 ± 23.03) | 0.059 | 0.433 |
| | FPG (94.83 ± 8.26) | 0.147 | 0.280 |
| | 1-h GCT (108.44 ± 31.21) | 0.392 | 0.071 |
| | 3-h (134.9 ± 119.5) | 0.577 | 0.133 |
| | GHb (5.23 ± 0.76) | 0.885 | 0.012 |

[a] Listed in descending order of the p value.
[b] 1-h GCT: the 1-hour plasma glucose concentration on the 50-gram glucose challenge test (mg/dL); 0-h OGTT: the fasting plasma glucose concentration on the oral glucose tolerance test (mg/dL); 1-h OGTT: the 1-hour plasma glucose concentration on the OGTT (mg/dL); 2-h OHGTT: the 2-hour plasma glucose concentration on the OGTT (mg/dL); 3-h OGTT: the 3-hour plasma glucose concentration on the OGTT (mg/dL); GPP: glycosylated plasma protein concentration (%); GHb: glycosylated hemoglo bin concentration (%); GSP: glycosylated serum protein concentration (%).

TABLE 2

Variables That Significantly Correlate with Infant Birthweight[a]

| Variable[b] (Means ± SD) Versus IBW[b] (Mean ± SD) | p Value | r Value |
|---|---|---|
| FPG (94.83 ± 8.26) 3532.98 ± 531.91 g | 0.000 | 0.937 |
| GPP (22.56 ± 1.48) 3532.98 ± 531.91 g) | 0.000 | 0.814 |
| 1-h GCT (108.44 ± 31.21 3532.98 ± 531.98 g | 0.000 | 0.509 |
| GHb (5.226 ± 0.759) 3532.98 ± 531.9 g | 0.005 | 0.370 |

[a] Listed in descending order of the p value.
[b] IBW: infant birth weight; FPG: fasting plasma glucose concentration (mg/dL); GPP: glycosylated plasma protein concentration (%); GSP: glycosylated serum protein concentration (%); 1-h GCT: 1 hour plasma glucose concentration on the 50-gram glucose challenge test (CGT) (mg/dL).

The results reported here demonstrate that a GPP concentration above 23% obtained at the same time that a GCT is performed at 24 to 28 weeks of gestation identifies infants at risk for macrosomia. At present, only those women who have a plasma glucose concentration above 140 mg/dL on the GCT go on to have an OGTT and thus have an FPG concentration determined. If the FPG concentration on the OGTT is greater than 90 mg/dL, the number of false-positive results is decreased, yielding the sensitivity and specificity of the GPP concentration greater than 23% plus FPG concentration greater than 90 mg/dL to 100% and 93%, respectively. Thus, if macrosomia is a concern, the time of the traditional GCT, in addition to the 1-hour plasma glucose concentration, FPG and GPP concentrations should be obtained. In summary, screening for macrosomia in the general population might be aided by combined analysis of GPP and FPG concentrations at 24 to 28 weeks of gestation.

REFERENCES

The teachings of the following references are incorporated by reference herein:

1. Third International Workshop-Conference on Gestational Diabetes Mellitus. Diabetes 1985; 34 (suppl 2):123–62.
2. Hadden, D. R. Geographic, ethnic, and racial variations in the incidence of gestational diabetes. Diabetes 1985; 34 (suppl 2):8–12.
3. Kitzmiller, J. L. Macrosomia in the infant of the diabetic mothers: characteristics, causes, prevention. In Jovanovic, L., Peterson, C. M., Fuhrmann, K. (eds); Diabetes and Pregnancy: Teratology, toxicology, and treatment. New York: Praeger Publishers, 1986:85–120.
4. Berkowitz, G. S., Roman, S. H., Lapinski, R. H, Alvarez, M. Maternal characteristics, neonatal outcome, and the time of diagnosis of gestational diabetes. Am. J. Obstet. Gynecol. 1992; 167: 976–82.
5. Gabbe, S. G. Gestational diabetes mellitus. N. Engl. J. Med. 1986; 315:1025–6.
6. Jovanovic, L., Peterson, C. M. Screening for gestational diabetes optimum timing and criteria for retesting. Diabetes 1985; 34 (suppl 2):21–3.
7. Shah, B. D., Cohen, A. W., May C., Gabbe, S. G. Comparison of glycohemoglobin determination and one-hour oral glucose screen in the identification of gestational diabetes. Am. J. Obstet. Gynecol. 1982; 144:774–7.
8. Huter, O., Drexel, H., Brezinka, C. et al. Low sensitivity of serum fructosamine as a screening parameter for gestational diabetes mellitus. Gynecol. Obstet. Invest. 1992; 34:20–3.
9. Nasrat, H. A., Ajabnoor, M. A., Ardawi, M. S. Fructosamine as a screening test for gestational diabetes mellitus: a reappraisal. Gynecol. Obstet. Invest. 1991; 34:27–33.
10. Cefalu, W. T., Prather, K. L., Chester, D. L. et al. Total serum glycosylated proteins in detection and monitoring of gestational diabetes. Diabetes Care 1990; 13:872–5.
11. Ryan, E. A., Strak, R., Crockford, P. M., Suthijumroon, A. Assessment of value of glycosylsated albumin and protein in detection of gestational diabetes. Diabetes Care 1987; 10:213–6.
12. Morris, M. A., Grandis, A. S., Litton, J. C. Longitudinal assessment of glycosylated blood protein concentrations in normal pregnancy and gestational diabetes. Diabetes Care 1986; 9:107–9.
13. Kurishita, M., Nakashima, K., Kozu, H. Glycated hemoglobin of fractionated erythrocytes, glycated albumin, and plasma fructosamine during pregnancy. Am. J. Obstet. Gynecol. 1992; 167:1372–8.
14. Aziz, N. L., Abdelwahab, S., Moussa, M., Georgy, M. Maternal fructosamine and glycosylated haemoglobin in the prediction of gestational glucose intolerance. Clin. Esp. Obstet. Gynecol. 1992; 19:235–41.
15. Sacks, D. A., Greenspoon, J. S., Fotheringham, N. Could the fasting glucose assay be used to screen for gestational diabetes? J. Reprod. Med. 1992; 37:907–9.
16. Williams, R. L., Creasy, R. K., Cunningham, G. C. et al. Fetal growth and perinatal viability in California. Obstet. Gynecol. 1982; 59:624–32.
17. Hays, W. B. Statistics. New York: Holt, Rinehart and Winston, 1963; 574–6.
18. Coustan, D. R. Maternal insulin to lower the risk of fetal macrosomia in diabetic pregnancy. Clin. Obstet. Gynecol. 1991; 34:288–95.
19. Jovanovic-Peterson, L., Peterson, C. M. Dietary manipulation as a primary treatment strategy for pregnancies complicated by diabetes. J. Am. Coll. Nutr. 1990; 9:320–5.

20. Neilson, D. R., Jr., Bolton, R. N., Prins, R. P. Glucose challenge testing in pregnancy. Am. J. Obstet. Gynecol. 1991; 164:1678–9.
21. Neiger, R., Coustan, D. R. The role of repeat glucose tolerance tests in the diagnosis of gestational diabetes. Am. J. Obstet. Gynecol. 1991; 165:787–90.
22. Super, D. M., Edelberg, S. C., Philipson, E. H. et al. Diagnosis of gestational diabetes in early pregnancy. Diabetes Care 1991; 14:288–94.
23. Narayanan, S. Laboratory monitoring of gestational diabetes. Ann. Clin. Lab. Sci. 1991; 21:392–401.
24. Fadel, H. E., Hammoud, S. D., Huff, T. A., Hays, R. J. Glycosylated hemoglobin in normal pregnancy and gestational diabetes. Obstet. Gynecol. 1979; 54:322–7.
25. Yatscoff, R. W., Mehta, A., Dran H. Cord blood glycosylated (glycated) hemoglobin: correlation with maternal glycosylated (glycated) hemoglobin and birth weight. Am. J. Obstet. Gynecol. 1988; 152:861–5.
26. Magee, M. S., Walden, C. E., Benedetti, T. J., Knopp, R. H. Influence of diagnostic criteria on the incidence of gestational diabetes and perinatal morbidity. JAMA 1993; 169:609–15.
27. Berkus, M. D., Langer, O. Glucose tolerance test: degree of glucose abnormality correlates with neonatal outcome. Obstet. Gynecol. 1993; 81:344–8.
28. Little, R. R., McKenzie, E. M., Shyken, J. M. et al. Lack of relationship between glucose tolerance and complications of pregnancy in nondiabetic women. Diabetes Care 1990; 13:483–7.
29. Skyler, J. S., O'Sullivan, M. J., Robertson, E. G. Blood glucose control during pregnancy. Diabetes Care 1980; 3:69–76.

We claim:

1. A method of diagnosing gestational diabetes mellitus in a female comprising the steps of:
   obtaining at least one blood sample from said female;
   determining in said blood sample the concentrations of fasting plasma glucose and glycosylated plasma protein; and
   determining if said concentrations equal or exceed predetermined threshold values as a diagnosis of gestational diabetes.

2. The method of claim 1, wherein said concentration of said fasting plasma glucose is expressed as a weight of said fasting plasma glucose per volume of blood plasma.

3. The method of claim 1, wherein said concentration of said glycosylated plasma protein is expressed as the percentage of total plasma protein that is glycosylated.

4. The method of claim 1, wherein said female has fasted overnight.

5. The method of claim 1, wherein said blood sample is obtained after a glucose challenge test.

6. The method of claim 5, wherein said glucose challenge test is a 1-hour 50-gram glucose challenge test.

7. The method of claim 1, wherein said blood sample is obtained at the 1-hour time point during an oral glucose tolerance test.

8. The method of claim 7, wherein said oral glucose tolerance test is a 3-hour 100-gram oral glucose tolerance test.

9. The method of claim 1, wherein said female has been pregnant from about 24 to 28 weeks.

10. The method of claim 1, wherein said concentration of said fasting plasma glucose is determined using a hexokinase method.

11. The method of claim 1, wherein said concentration of said glycosylated plasma protein is determined by boronate-affinity high-performance liquid chromatography.

12. The method of claim 1, wherein said concentration of said fasting plasma glucose equals or exceeds a predetermined threshold value of 90 mg/dL.

13. The method of claim 1, wherein said concentration of said glycosylated plasma protein equals or exceeds a predetermined threshold value of 23%.

14. The method of claim 1 wherein said concentrations of said fasting plasma glucose and said glycosylated plasma protein equals or exceeds predetermined threshold values of 90 mg/dL and 23%, respectively.

15. A method of diagnosing gestational diabetes mellitus in a female comprising the steps of:
   obtaining a blood sample from said female;
   determining in said blood sample the concentration of glycosylated plasma protein; and
   determining if said concentration equals or exceeds a predetermined threshold value as a diagnosis of gestational diabetes.

16. The method of claim 15, wherein said concentration of said glycosylated plasma protein is expressed as the percentage of total plasma protein that is glycosylated.

17. The method of claim 15, wherein said female has fasted overnight.

18. The method of claim 15, wherein said blood sample is obtained after a glucose challenge test.

19. The method of claim 18, wherein said glucose challenge test is a 1-hour 50-gram glucose challenge test.

20. The method of claim 15, wherein said blood sample is obtained at the 1-hour time point during an oral glucose tolerance test.

21. The method of claim 20, wherein said oral glucose tolerance test is a 3-hour 100-gram oral glucose tolerance test.

22. The method of claim 15, wherein said female has been pregnant from about 24 to 28 weeks.

23. The method of claim 15, wherein said concentration of said glycosylated plasma protein is determined by boronate-affinity high-performance liquid chromatography.

24. The method of claim 15, wherein said concentration of said glycosylated plasma protein equals or exceeds a predetermined threshold value of 23%.

* * * * *